United States Patent [19]
Murphy et al.

[11] Patent Number: 5,864,641
[45] Date of Patent: Jan. 26, 1999

[54] OPTICAL FIBER LONG PERIOD SENSOR HAVING A REACTIVE COATING

[75] Inventors: Kent A. Murphy, Troutville; Mark E. Jones, Blacksburg, both of Va.

[73] Assignee: F&S, Inc., Blacksburg, Va.

[21] Appl. No.: 838,873

[22] Filed: Apr. 11, 1997

[51] Int. Cl.$^6$ .................................. G02B 6/00; G01J 1/04
[52] U.S. Cl. ................................. 385/12; 385/15; 385/37; 385/123; 385/126; 385/127; 385/141; 250/227.14; 250/227.18; 250/227.23
[58] Field of Search .................................. 385/12, 13, 15, 385/37, 123, 125, 126, 127, 141; 250/227.14, 227.18, 227.23

[56] References Cited

U.S. PATENT DOCUMENTS

| | | | |
|---|---|---|---|
| 4,815,843 | 3/1989 | Tiefenthaler et al. | 356/128 |
| 4,929,049 | 5/1990 | Le Goullon et al. | |
| 5,026,139 | 6/1991 | Klainer et al. | |
| 5,047,213 | 9/1991 | Finlan et al. | |
| 5,173,747 | 12/1992 | Bolarski et al. | |
| 5,210,404 | 5/1993 | Cush et al. | 385/37 X |
| 5,253,037 | 10/1993 | Klainer et al. | |
| 5,280,172 | 1/1994 | Di Bin et al. | 250/227.21 |
| 5,324,933 | 6/1994 | Berkcan | 385/12 X |
| 5,359,680 | 10/1994 | Riviere | |
| 5,430,817 | 7/1995 | Vengsarkar | |
| 5,492,840 | 2/1996 | Malmqvist et al. | |
| 5,641,956 | 6/1997 | Vengsarkar et al. | |
| 5,646,400 | 7/1997 | Perez et al. | 250/227.18 |
| 5,647,039 | 7/1997 | Judkins et al. | 385/37 |
| 5,757,540 | 5/1998 | Judkins et al. | 359/341 |

OTHER PUBLICATIONS

V. Bhatia et al., "Optical Fiber Long–Period Grating Sensors," *Lightnews*, Winter 1995, pp. 6–11.

T.A. Tran et al., "Real–time immunoassays using fiber optic long–period grating sensors," *Biomedical Sensing, Imaging, and Tracking Technologies I*, Proceedings SPIE—The International Society for Optical Engineering, R.A. Lieberman et al., Eds., vol. 2676, Jan. 29–31, 1996, pp. 165–170.

A.M. Vengsarkar et al., "Long–Period Fiber Gratings as Gain–Flattening and Laser Stabilizing Devices," *Tenth International Conference on Integrated Optical Fibre Communication*, vol. 5, Jun. 26–30, 1995, pp. 3–4.

A.M. Vengsarkar et al., "Long–Period Fiber Gratings as Band–Rejection Filters," *Journal of Lightwave Technology*, vol. 14, No. 1, Jan. 1996, pp. 58–65.

A.M. Vengsarkar et al., "Long–Period Cladding–Mode–Coupled Fiber Gratings: Properties and Applications," *1995 Technical Digest Series*, vol. 22, Sep. 9–11, 1995, pp. SaB2–1–SaB2–4.

A.M. Vengsarkar et al., "Long–Period Gratings as Band–Rejection Filters," *OFC '95*, Feb. 26–Mar. 3, 1995, pp. PD4–1–PD4–5.

E. Stenberg et al., "Quantitative Determination of Surface Concentration of Protein with Surface Plasmon Resonance Using Radiolabeled Proteins," *Journal of Colloid and Interface Science*, vol. 143, No. 2, May 1991, pp. 513–526.

L. De Maria et al., "Fiber–optic sensor based on surface plasmon interrogation," *Sensors and Actuators*, B. 12, Dec. 21, 1992, pp. 221–223.

R.C. Jorgenson et al., "A fiber–optic chemical sensor based on surface plasmon resonance," *Sensors and Actuators*, B. 12, Dec. 20, 1992, pp. 213–220.

*Primary Examiner*—Brian Healy
*Attorney, Agent, or Firm*—Joy L. Bryant

[57] ABSTRACT

An optical sensor is provided. The optical sensor comprises an optical waveguide, at least one long period grating disposed within the optical waveguide and a reactive coating positioned in an operable relationship to the long period grating wherein the reactive coating causes the long period grating to produce a wavelength transmission spectrum functionally dependent on a parameter sensed. Such sensors may be used to measure physical, electrical and chemical parameters within a single system.

23 Claims, 6 Drawing Sheets

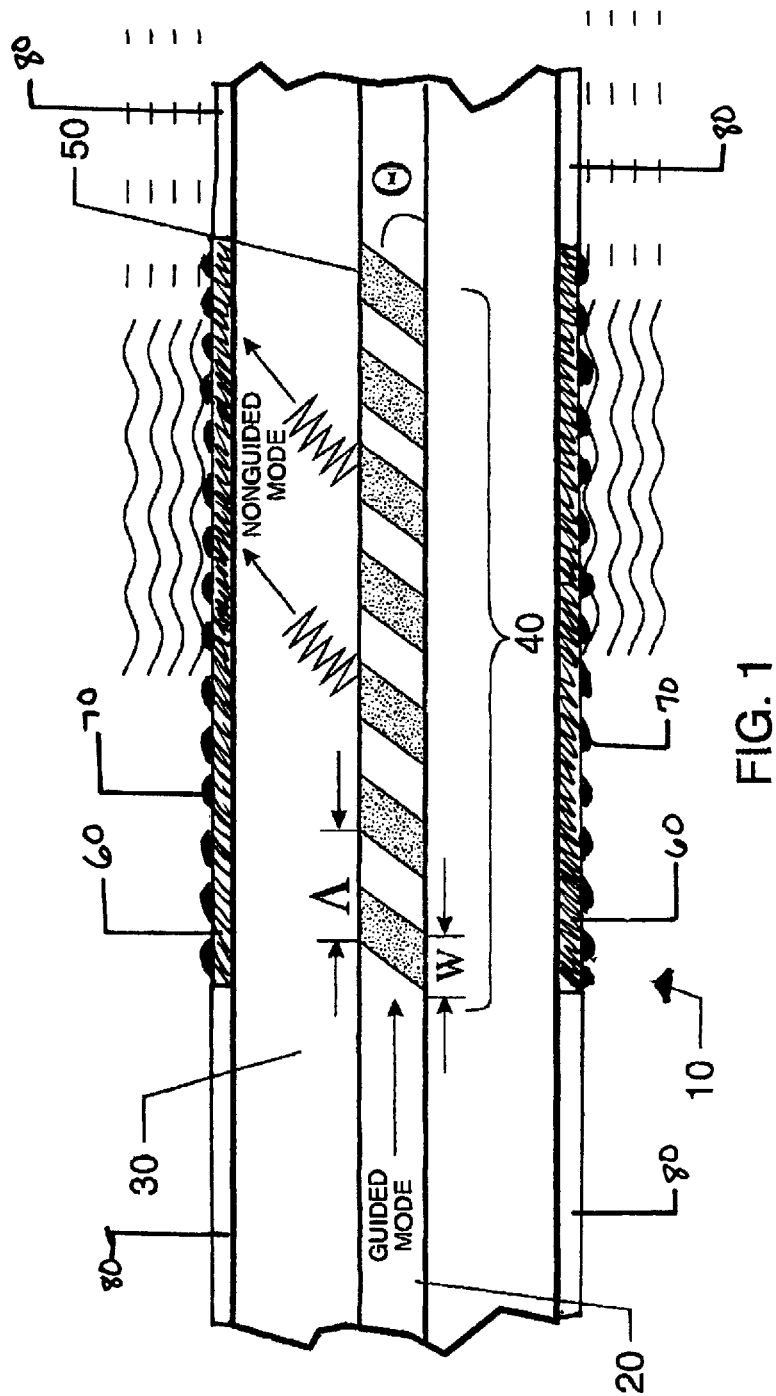

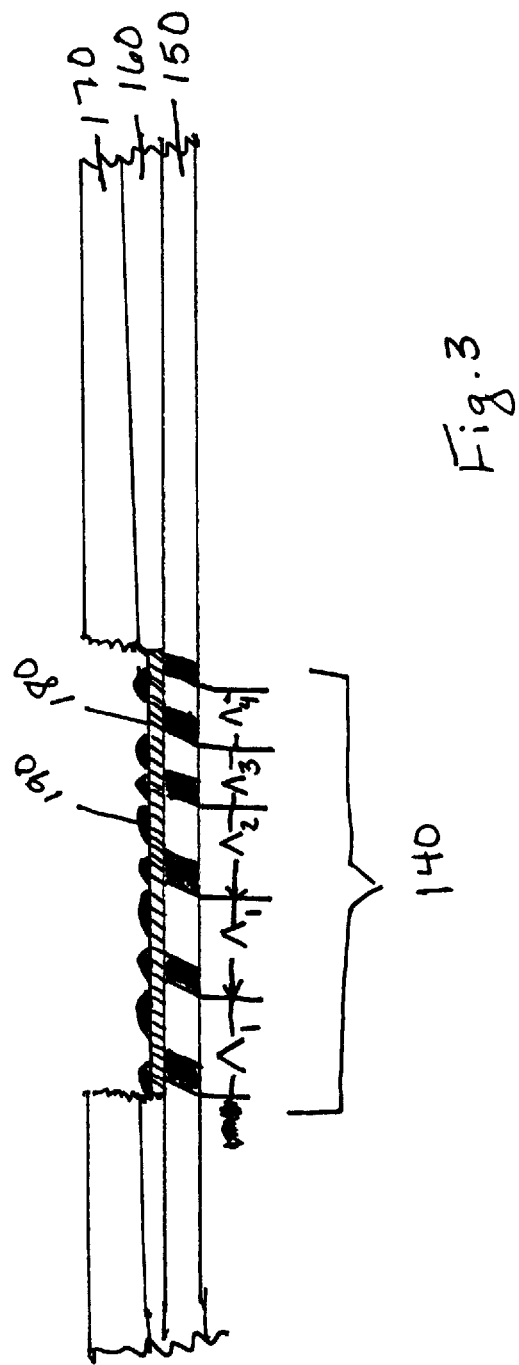

OPTICAL FIBER LONG PERIOD SENSOR HAVING A REACTIVE COATING

FIELD OF THE INVENTION

The present invention relates to optical sensors. In particular, it relates to optical sensors comprising a waveguide, a long period grating, and a reactive coating.

BACKGROUND OF THE INVENTION

The ability to detect various physical and electrical activities along with the presence of certain substances in certain systems is desirable for not only medical diagnosis but also for process control, environmental monitoring, and for general real-time chemical and biological analysis. Current optical sensing approaches for biological and chemical measurements are based on fluorescence and surface plasmon resonance (SPR) techniques. However, these techniques have been found to be cumbersome and lack in sensitivity. In addition, these approaches fail to account for measuring certain physical and electrical changes which may be occurring in the system.

Optical sensors based on fluorescence require multiple fibers or tapering of an optical fiber prior to applying an affinity coating. Light propagating in the tapered region of the optical fiber has an evanescent field that extends into the coating. A sample having an unknown concentration of specific biological agents is doped with a fluorescent dye that is excited by the evanescent signal wavelength. The specimen is adsorbed by the coating and the fluorescent signal of the biological agents is coupled back into the fiber. The magnitude of the fluorescent signal is an indication of the specimen concentration.

It has been found that the manufacturing of these sensors is labor-intensive and not cost-effective because the optical fiber must be tapered. There is no alternative to tapering the fiber because the wavelength of the excitation and fluorescent signal are such that propagation of the fluorescent signal in the fiber is lossy. Tapering the optical fiber reduces some of this loss mechanism but weakens the structural integrity and thus, severely limits field use. In addition, these sensors have limited signal-to-noise ratios due to the background fluorescence of non-bound agents. Since the interrogation of the device determines fluorescent intensity, fluctuations due to background signals create errors in the measurement. In turn, the sensitivity of these sensors is much less than the sensitivity of the sensors of the present invention.

Bulk SPR-based techniques are difficult to transition into a mobile platform because critical component alignment cannot be maintained in a field environment. To ruggedize the system, impractical size and weight restrictions are required. Optical fiber-based SPR sensors have been made but they have many limitations. In SPR, an optical transverse magnetic (TM) wave is coupled to a surface wave which is created in a metallic layer such as gold. SPR wave excitation occurs due to the evanescent field created by an incident wave totally internally reflected (TIR) at a metal interface. The energy level of the metal electron gap spacing must correspond to the excitation wavelength of the evanescent field. If TIR or other stimulation properly matches the momentum and propagation direction of the incident and SPR signal, excitation will occur and hence absorption of that particular wavelength. When it is desirable to determine biological or chemical concentration, an affinity coating is applied to the non-excitation side of the metallic layer. When adsorption occurs, the refractive index of the sample changes which results in a change in the surface plasmon excitation conditions. The shift in the absorption wavelength is then monitored to determine refractive index changes which are correlated to chemical or biological agent concentration.

Single mode fiber, when used for SPR, does not guarantee transverse magnetic (TM) light propagation. Thus the polarization of light in low-birefringence fiber needs to be adjusted until an SPR wave is excited. Although such polarization control works well in the laboratory environment, in field applications the polarization is difficult to maintain when the fiber is perturbed during sensing. When multimode fiber is used, both TM and transverse electric (TE) modes are propagated. However, due to the geometry of the propagating modes, the maximum coupling of TM light is 50% or 3 dB. Thus, only one-half of the input light can possibly excite an SPR wave. The isolation of the absorption band of the SPR signal is a theoretical maximum 3 dB, and in practical systems it is typically 1.8 dB due to the relatively small evanescent fields in lower-order modes. The isolation of the absorption band of a long period grating, used in the present invention, is typically 25 dB down from the peak spectral signal. When specifically designed optical fiber and gratings are used, the isolation of the absorption band has a potential of greater than 35 dB down from the peak spectral signal.

A mode scrambler is required for SPR sensors to ensure that all modes are excited equally. Each mode will have a different sensitivity and when a spectral shift occurs due to the refractive index change of a test specimen, the spectral shape of the absorption signal changes. This shape change leads to detection errors through misinterpretation of absorption band location. Optical waveguide sensors based on long period gratings generate significantly larger signal-to-noise ratios allowing for the determination of the long period grating coupling wavelength to be more accurate and accomplished with simpler demodulation electronics. Moreover, the shape of the long period grating does not change when shifting.

SPR sensors, in general, operate at the same wavelength for similar biosample evaluation. Complex optical or mechanical switching is needed to monitor multiple sensors with a single source/detector system. This reduces the reliability of the device by introducing additional mechanical elements as well as increasing the overall cost of the system. The long period grating sensors of the present invention couple at wavelengths determined by the long period gratings written in the waveguide using high energy ultraviolet light. These periodic index variations are written with different spacings to long period gratings of different wavelengths. The long period grating can therefore be demodulated using standard wavelength division multiplexing techniques. However, SPR sensors and fluoroscopy sensors are limited to specific absorption and fluorescent wavelengths.

The long period grating based sensors of the present invention are easily manufactured. When SPR optical fiber probes are produced, the cladding must be stripped to precise dimensions. The region must be radially symmetric throughout so the light within the fiber maintains a constant propagation angle. Next, a metallic layer must be coated onto the stripped region at a thickness that is radially symmetric. If the thickness of the metallic layer varies, the SPR coupling conditions change and thus reduce sensitivity. The precision involved in making these sensors makes it difficult to manufacture them in large quantities. The long period grating based sensors of the present invention are made consistently and accurately through exposure to a high energy UV signal. The signal is generated by illumination of an amplitude mask.

Tran et al. ("Real-Time Immunoassays Using Fiber-Optic Long-Period Grating Sensors", *Biomedical Sensing, Imaging, and Tracking Technologies I*, Proceedings SPIE—The International Society for Optical Engineering, R. A. Lieberman et al., Eds., Vol. 2676, Jan. 29–31, 1996, pp. 165–170) demonstrated how a long-period grating was used to detect and monitor in real time the interaction of a specific antigen to an immobilized antibody on a silica fiber. Long-period gratings optically couple the fundamental guided mode to discrete cladding modes that attenuate rapidly on propagation along the length of an optical fiber. Any change in the properties of the cladding or the material surrounding the cladding, modifies the coupling mechanism and results in a modulation of the output optical spectrum. If a broadband light source is injected into the optical fiber, the attenuation spectra arising from the coupling to different cladding modes suitably modifies the original spectral profile. Long period grating based biosensors utilize the sensitivity to the index of refraction variation in the medium enclosing the cladding as a means of monitoring serological interactions. In their experiments, the antibody was adsorbed to the silica optical fiber. As toxin A complexes with the antibodies, the molecular length of the entire compound increases and the density of the bound molecules increases thus changing the refractive index.

However, this system was found to be deficient and the test results are questionable. Unfortunately, Tran et al. failed to run a control so there is no way to determine what caused the change in wavelength. In turn, the changes in output may have resulted from non-bonding interactions. When the antibodies are adhered directly to an optical fiber, the antibody density is limited by the antibody size. The density affects the number of target molecules that can be captured and also the refractive index of the coating. To obtain measurable sensitivity from the antibodies, the population of attached antibodies must be as large as possible. This is counter-productive because the large population results in the refractive index of the coating becoming too large to be useful. Antibodies have two sites for binding to target molecules. When antibodies are applied to an optical fiber, they are packed too close together causing the binding sites of adjacent antibodies to be positioned close together. This results in the overlap of binding sites, which precludes potential binding with the target molecules. The close packing of the binding sites prevents capture by either site. In addition, many of the binding sites are oriented toward the fiber instead of toward the sample, reducing the overall number of binding sites. Lastly, the target molecule (protein) that the antibodies on the fiber are trying to capture is typically greater than the antibody spacing. In turn, antibodies end-up competing for capture and no binding occurs with the coating.

An object of the present invention is to provide an optical sensor having a reactive coating.

Another object of the present invention is to provide an optical sensor having a waveguide and a long period grating wherein a reactive coating which is positioned in an operable relationship to the long period grating such that the reactive coating causes the long period grating to produce a wavelength transmission spectrum functionally dependent on the parameter sensed.

Another object of the invention is to provide an optical sensor which is more sensitive than SPR or fluoroscopy.

Another object of the invention is to provide an optical sensor which does not require metal on a waveguide surface.

Another object of the invention is to provide an optical sensor which has at least one long period grating disposed within an optical waveguide and a reactive coating which is either physically reactive, electrically reactive or chemically reactive.

SUMMARY OF THE INVENTION

By the present invention, an optical sensor is provided. The optical sensor comprises an optical waveguide, at least one long period grating disposed within the optical waveguide and a reactive coating positioned in an operable relationship to the long period grating wherein the reactive coating causes the long period grating to produce a wavelength transmission spectrum functionally dependent on a sensed parameter. The reactive coating is either physically reactive, electrically reactive or chemically reactive. For the purpose of this specification and the appended claims, a reactive coating is defined as a coating capable of undergoing a change when exposed to a specific parameter such that it causes the long period grating to produce a wavelength transmission spectrum functionally dependent on the change which takes place. A physically reactive coating is sensitive to either pressure, temperature, strain or shape. Thus, when a pressure sensitive coating is exposed to a change in pressure, the wavelength transmission spectrum changes. In addition, an electrically reactive coating is sensitive to changes in magnetic fields or conductivity of electrons. Lastly, chemically reactive coatings undergo chemical reactions when exposed to various substances. Some chemically reactive coatings have exposed active sites which, when the exposed active sites react with a target material, the optical characteristics of the coating change, thus yielding a different wavelength transmission spectrum. In turn, the active sites are capable of reacting with the substances to which they are exposed causing either a chemical binding reaction or a physical change in the coating such as swelling or erosion, which effects the wavelength transmission spectrum.

The operable relationship of the reactive coating to the long period grating is defined by the place where light is coupled. The reactive coating may be slightly in front of the long period grating and extending along a portion of or the entire length of the long period grating; directly across from and extending along a portion of or the entire length of the long period grating; or covering only a portion of the long period grating.

The optical waveguide is any optical waveguide known to those skilled in the art and, in particular, a planar optical waveguide, an integrated optic waveguide, or a fiber optic waveguide. Most preferably, the optical waveguide is a fiber optic waveguide having a core, a cladding surrounding the core, and at least one long period grating disposed within the core. For fiber optic waveguides, the reactive coating is disposed either on the cladding or on the core.

The long period grating of the present invention has at least one but preferably a plurality of index perturbations of width w spaced apart by a periodic distance $\Lambda$ where $10 \; \mu m \leq \Lambda \leq 1500 \; \mu m$. The periodic distance may be either regular or irregular.

An optical sensor is provided which comprises an optical waveguide, a plurality of long period gratings disposed within the optical waveguide, and a plurality of reactive coatings positioned in an operable relationship to the long period gratings. Preferably, each reactive coating causes the long period grating to produce a wavelength transmission spectrum functionally dependent on each parameter sensed.

As a preferred embodiment, an optical sensor comprises a fiber optic waveguide having a core, a cladding surrounding the core, and at least one long period grating disposed within the core; and a reactive coating disposed on the cladding and positioned in an operable relationship to the long period grating wherein the reactive coating causes the long period grating to produce a wavelength transmission spectrum functionally dependent on a parameter sensed.

As another preferred embodiment an optical sensor comprises a fiber optic waveguide having a core, a cladding surrounding the core and a plurality of long period gratings disposed within the core; and a plurality of reactive coatings, each coating disposed on the cladding and positioned in an operable relationship to each long period grating. Each reactive coating causes the long period grating to produce a wavelength transmission spectrum functionally dependent on each parameter sensed.

DETAILED DESCRIPTION OF THE INVENTION

Figure 2:
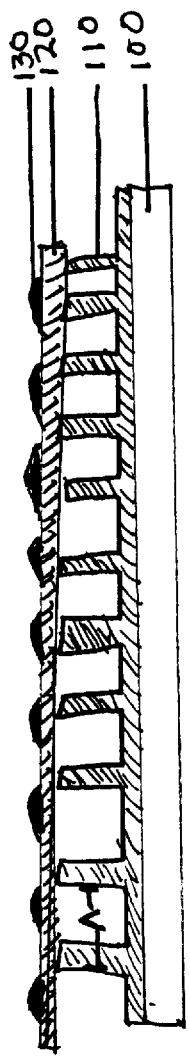
FIG. 2 is a schematic cross-section of a planar optic waveguide having a reactive coating disposed directly on the long period grating.

The invention is an optical sensor comprising a waveguide, at least one long period grating disposed within the waveguide, and a reactive coating placed in an operable relationship to the long period grating such that the reactive coating causes the long period grating to produce a wavelength transmission spectrum functionally dependent on a parameter sensed. The reactive coating is any reactive coating known to those skilled in the art and is sensitive to either physical, electrical or chemical changes. A physically reactive coating is one which is sensitive to pressure, temperature, strain or shape. For example, a change in pressure alters the reactive coating such that it affects the wavelength transmission spectrum produced by the long period grating. A similar effect is seen for an electrically reactive coating where exposure to a magnetic field causes a change in the coating and affects the wavelength transmission spectrum. Lastly, a chemically reactive coating undergoes a chemical change when exposed to certain target materials. This reaction may either change the chemical or the physical make-up of the coating. For example, when the chemically reactive coating has target sites present, a chemical bond is formed between the target site and a specific molecule. Alternatively, some chemically reactive coatings undergo physical changes such as swelling or erosion when contact is made with certain chemical substances. In all instances, there is a change in the wavelength transmission spectrum produced by the long period grating which results from exposure of the reactive coating to certain substances.

One such coating is simply a concentrated solution of a material having active sites, such as antibodies, which is deposited directly on the waveguide so the active sites are attached directly from the waveguide. As an alternative, the coating is a complex formulation having other materials compounded along with the material with the active sites such that the active sites are attached within the coating. In particular, the reactive coating has reactive chemical sites such as low molecular weight ligands. The coating is deposited on the waveguide and the active sites are oriented away from the waveguide so they are able to complex with specific target molecules. Another type of coating is a compounded coating having active sites within the coating which are capable of changing the physical properties of the coating when the coating comes into contact with a specific material. One example is a coating which is solvated by a specific solvent, thus causing the thickness of the coating to change which ultimately changes the coating's refractive index profile. Another example of a reactive coating is one which has active sites which bond with fluorescent dyes. Although the examples presented are based on chemically reactive coatings, the actual composition of the reactive coating is immaterial provided that the reactive coating causes the long period grating to produce a wavelength transmission spectrum functionally dependent on a specific parameter which is sensed.

For those reactive coatings having active sites, the active sites are preferably oriented away from the optical waveguide. Most preferably, the active sites are oriented outward towards the sample to be tested.

Figure 1:
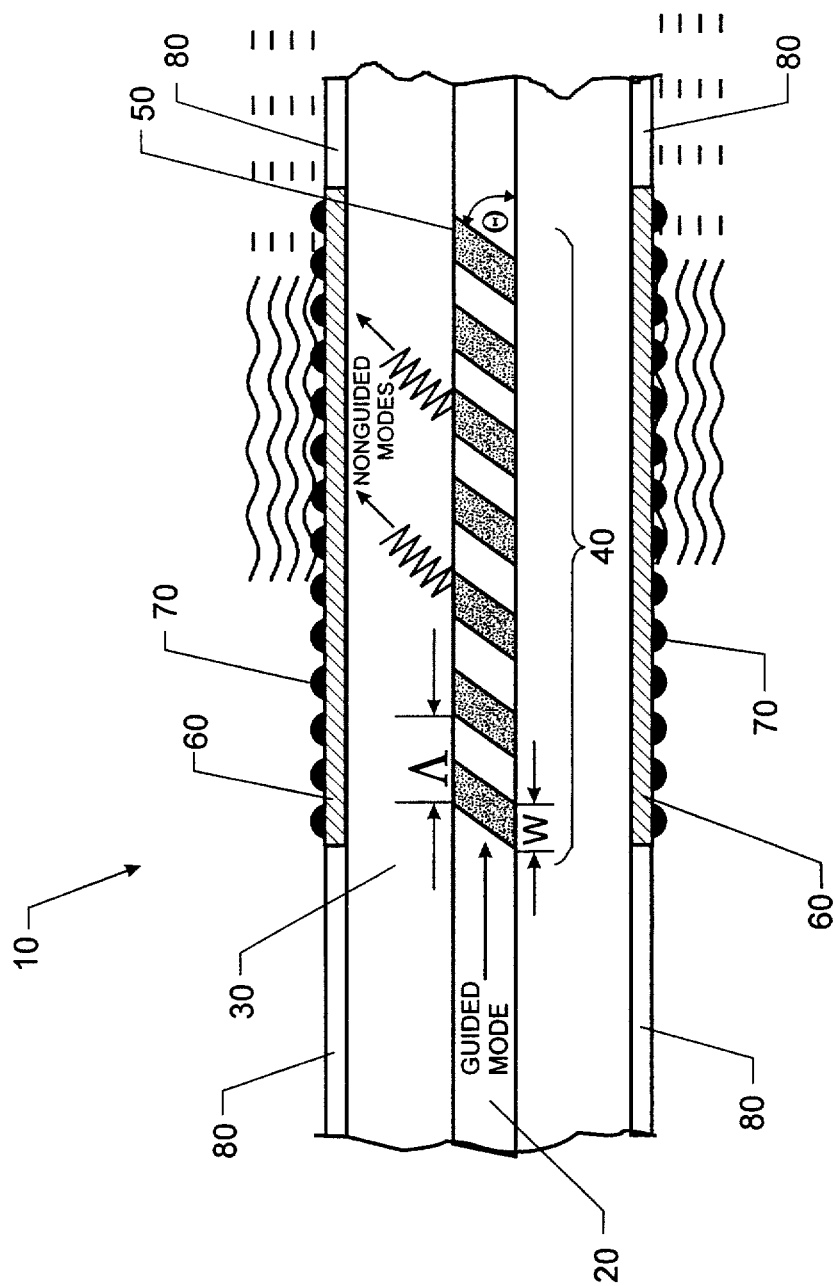
FIG. 1 is a schematic cross-section of a fiber optic waveguide having a reactive coating disposed on the cladding.
Figure 2:
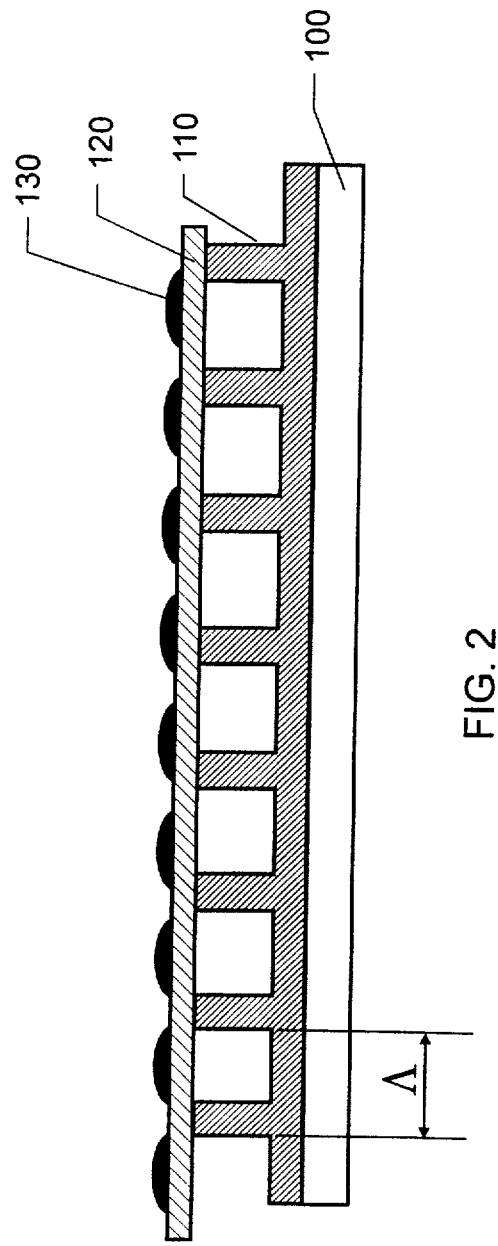
Figure 3:
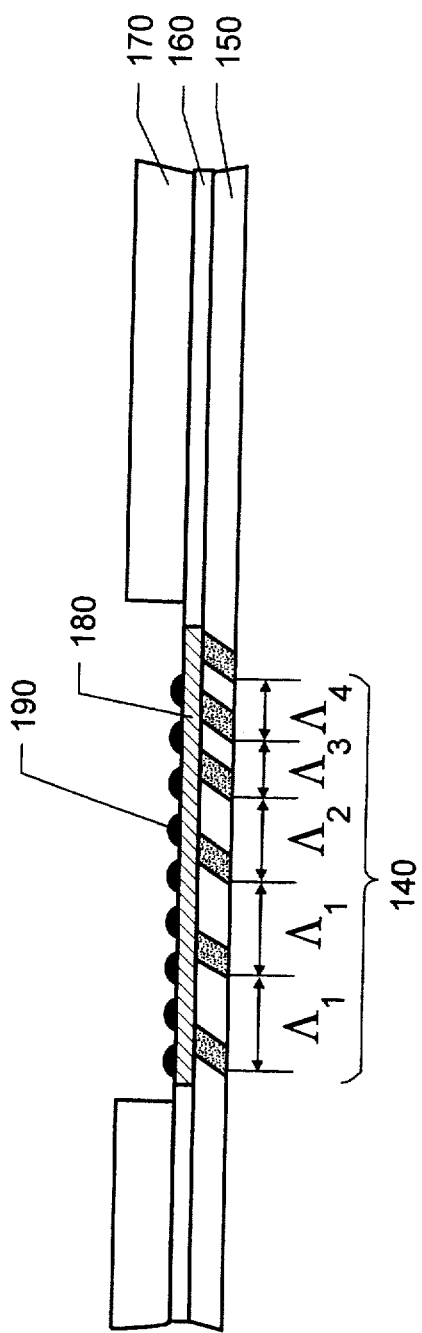
FIG. 3 is a schematic cross-section of a fiber optic waveguide having an irregular periodicity and having a reactive coating disposed on the core.
Figure 4:
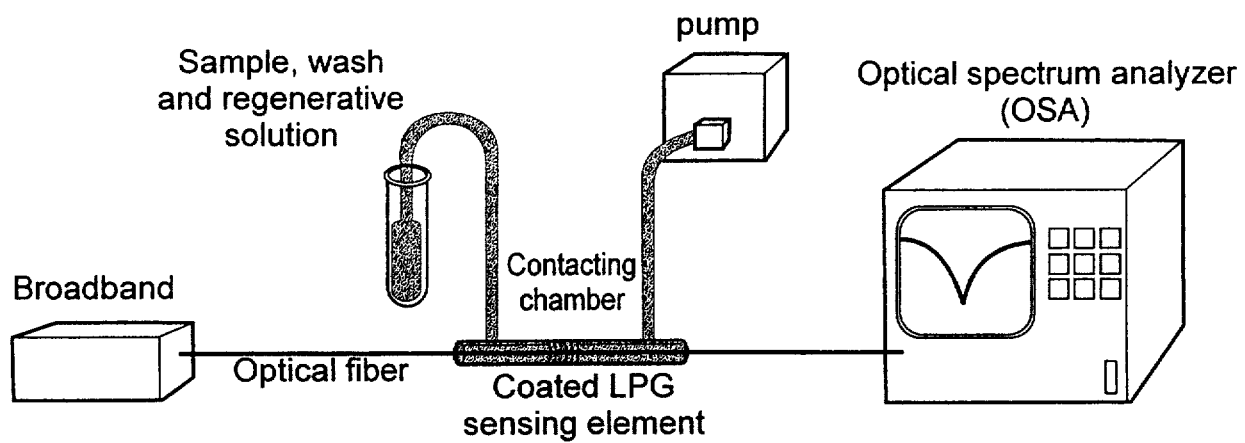
Figure 5:
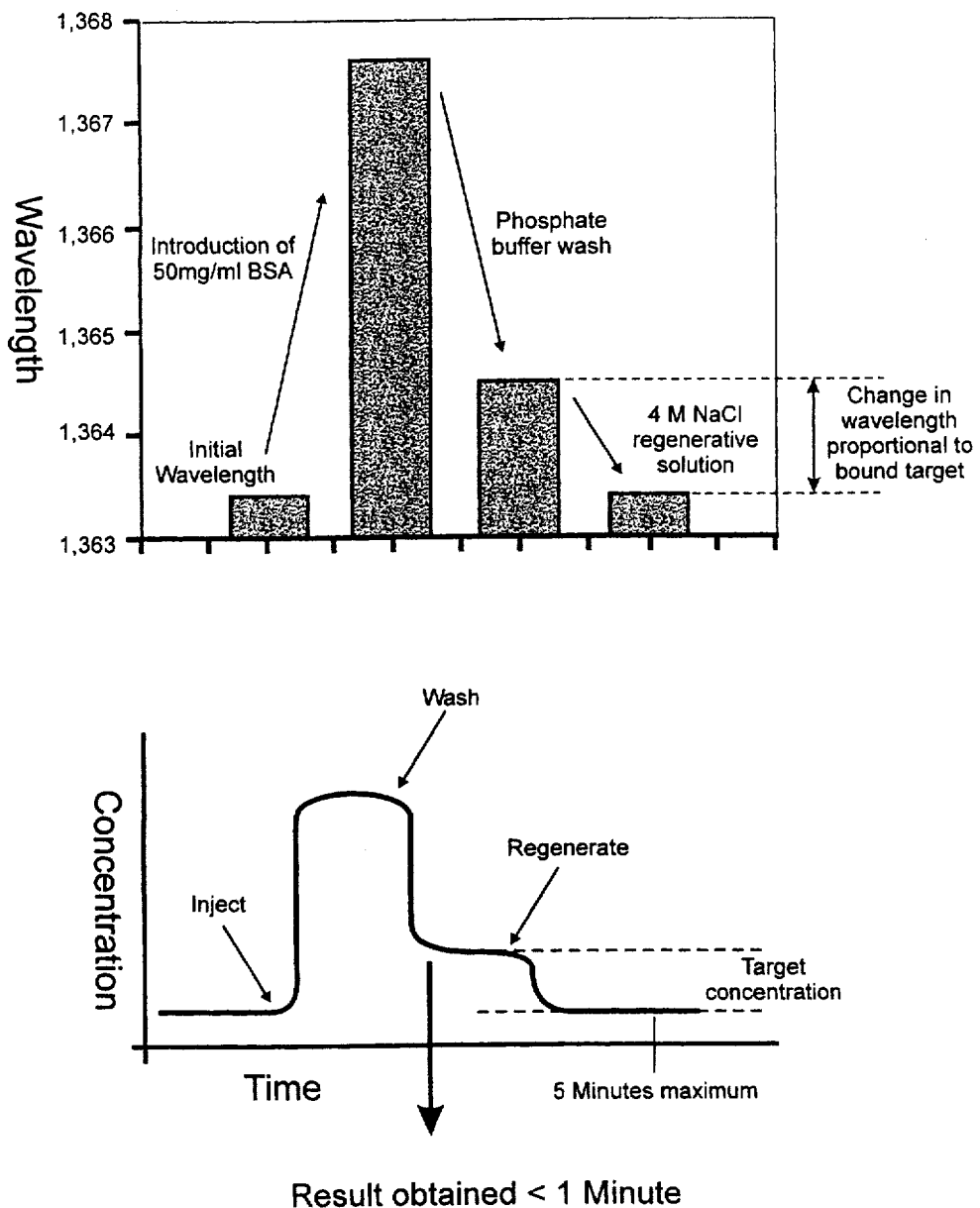
Figure 6:
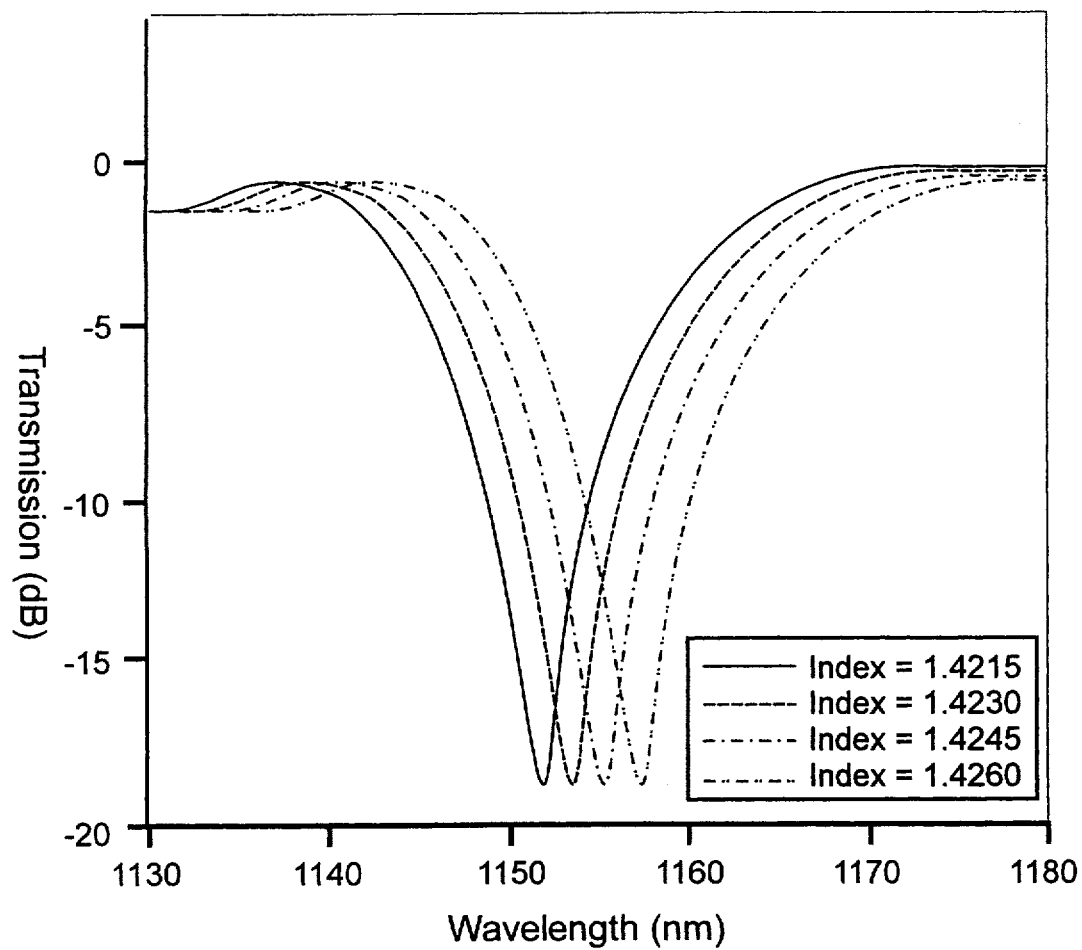

The optical waveguides of the present invention have at least one long period grating disposed within the optical waveguide. In the simplest arrangement, the optical waveguide has only one long period grating with one reactive coating placed in an operable relationship to the long period grating wherein the reactive coating causes the long period grating to produce a wavelength transmission spectrum functionally dependent on a parameter sensed. An example of a preferred embodiment of the present invention is shown in FIG. 1, wherein the optical waveguide is a fiber optic waveguide 10. The fiber optic waveguide is comprised of a core 20, a cladding 30 surrounding the core, and a long period grating 40 disposed within the core. The long period grating 40 has a plurality of index perturbations of width w spaced apart by a periodic distance $\Lambda$ where $10 \ \mu m \leq \Lambda \leq 1500 \ \mu m$. The periodic distance is spaced at regular intervals or irregular intervals. Such irregular periodic distances are shown in FIG. 3, where $\Lambda_1 \geq \Lambda_2 \geq \Lambda_3 \geq \Lambda_4$.

Referring back to FIG. 1, light launched in the waveguide core 20 interacts with the long period grating 40 and is converted into a number of modes contained within the waveguide cladding 30. These cladding modes propagate over short distances in the cladding 30 before being attenuated by the boundary between the cladding and the protective coating 80 and bends in the fiber. A reactive coating 60 is disposed on the cladding 30 in an operable relationship to the long period grating 40 such that the reactive coating is chemical in nature and has exposed active sites 70 which are oriented away from the fiber. When coupling occurs, the long period grating produces a wavelength transmission spectrum which reflects this. If no coupling occurs, there is no change in the wavelength transmission spectrum.

When the exposed active sites contact a specific chemical or biological agent, there is a change in the density of the coating which alters the cladding mode's effective refractive index. This change effects a change in the coupling conditions of the guided modes to the non-guided modes and causes a shift in the position of the resonance absorption band. The coupling wavelength shifts are indicative of refractive index changes which are directly related to changes in the coating itself. Thus, the sensing mechanism of the invention is different from that of SPR or fluoroscopy. Moreover, long period gratings without reactive coatings are sensitive to all refractive index changes that occur in the test specimen. Thus, the reactive coating allows the sensor to be environmentally specific.

FIG. 2 shows a cross sectional view of an alternative embodiment of the present invention, wherein the optical waveguide is a planar optical waveguide or an integrated optic waveguide. Such a waveguide is two-dimensional in configuration in contrast to the three dimensional configuration of a fiber optic waveguide. In a planar optical waveguide, the long period grating 110 is disposed on a planar substrate 100 using stereolithography or any other method known to those skilled in the art. A reactive coating 120, and in this case it is a chemically reactive coating, is deposited as a top coat over the long period grating 110 such that the coating's exposed active sites 130 are oriented away from the waveguide.

FIG. 3 depicts a cross section of a fiber optic waveguide wherein the cladding 160 and the protective coating 170 are stripped to expose the core 150 and the reactive coating 180 is disposed on the core 150. The long period grating 140 has irregular periodic distances. The reactive coating has active sites 190 which are oriented away from the fiber.

As an alternative embodiment, the optical sensor has a plurality of long period gratings disposed within a waveguide and a plurality of reactive coatings positioned in an operable relationship to the long period gratings. The reactive coatings are different so as to measure for different chemical and physical parameters present in the sample. For example, an optical waveguide having five long period grating sites, has four different reactive coatings applied to the waveguide. In this example, two of the optically reactive coatings are the same and applied to two different sites where the other three coatings are each different. The two coatings which are the same are pressure sensitive; the third coating has a target specific to a certain substance; a fourth coating swells when it reacts with a particular substance; and a fifth coating is sensitive to a certain magnetic field. Alternatively, the optically reactive coating is different at each site.

The optical waveguide is either a planar optical waveguide, an integrated optic waveguide or a fiber optic waveguide. Most preferably, the optical waveguide is a fiber optic waveguide having a core, a cladding surrounding the core and at least one long period grating disposed within the core. The reactive coating is disposed either on the cladding or on the core. As another embodiment, the optical sensor comprises a fiber optic waveguide having a core, a cladding surrounding the core and a plurality of long period gratings disposed within the core. Each reactive coating is disposed on the cladding and positioned in an operable relationship to each long period grating such that each long period grating produces a wavelength transmission spectrum functionally dependent on each parameter sensed.

For those reactive coatings which are chemically reactive and have exposed active sites, the orientation of the exposed active sites is controlled in several ways. One method which is used to control the orientation of active sites for antibody-antigen complexes is to use low molecular weight species. It was discovered that the antibodies used by Tran et al. failed to be operable because of the large molecular weights involved. As the antibodies bound with the target molecules, the refractive index of the coating became too large to be of any use. Thus, by the present invention, in order to solve this problem, a lower molecular weight species is used to coat the cladding and allows for the orientation of the antibody to be away from the fiber. Another method is to provide a coating with active sites which are bound within the coating instead of directly to the fiber.

The following examples illustrate the preparation and use of the optical sensor. These examples are merely illustrative and intended to enable those skilled in the art to practice the invention in all of the embodiments flowing therefrom, and do not in any way limit the scope of the invention as defined by the claims.

EXAMPLES

Example 1

Hydrogen-loaded optical fibers were exposed to 244 nm UV radiation from a frequency-doubled Argon-Ion laser, through a chrome-plated amplitude mask possessing a periodic rectangular transmittance function used to fabricate a long period grating based fiber optic sensor. The typical writing times for a CW laser with power of 120 milliwatts is 30 to 40 minutes for different fibers. The laser is typically scanned across a 1.5 to 2.5 cm length during this time frame. For coupling to the highest-order cladding mode, the maximum isolation (loss in transmission intensity) was in the 5 to 20 dB range on wavelengths depending on the fiber parameters, duration of UV exposure, and mask periodicity. The desired fundamental coupling wavelength is easily varied by using an inexpensive amplitude mask of different period, $\Lambda$. The insertion loss and back-reflection of a typical index discontinuity was 0.2 dB and –80 dB respectively. The fiber was then coated with a coating whose refractive index was 1.37. The coating was 100 nm thick. The coating was populated with reactive sites for the binding of protein.

Example 2

The fiber of Example 1 was washed with 25 mM sodium phosphate, pH 7.2 (phosphate buffer), 4M NaCl, 0.5M NaOH, and a phosphate buffer. A baseline wavelength of 1363.4 nm was observed in phosphate buffer.

Figure 4:
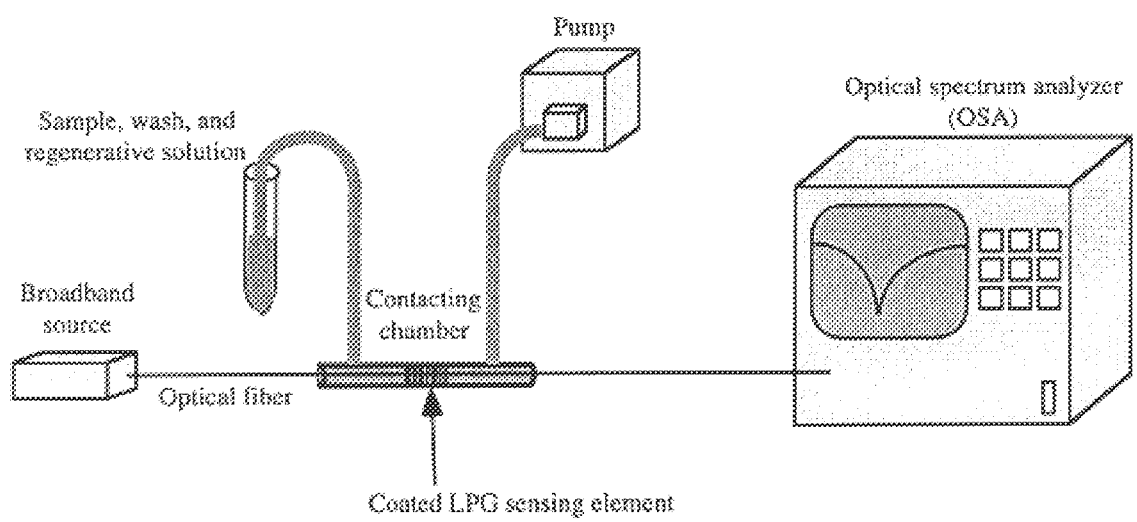
FIG. 4 is a schematic showing an experimental setup used to test the optical sensor of the present invention.

In order to observe the optical reactivity of the coating, the fiber of example 1 was challenged with a 50 mg/ml solution of bovine serum albumin (BSA) in phosphate buffer and subject to the experimental set-up shown in FIG. 4. A wavelength of 1367.55 nm was measured for the BSA solution. After extensive washing of the fiber with phosphate buffer, the peak shifted to 1364.5 nm, a 1.1 nm shift from the baseline. This shift corresponded to a $2.25 \times 10^{-3}$ change in the index of refraction, which indicates that a maximum of 6.4 ng of BSA bound to the fiber.

Figure 5:
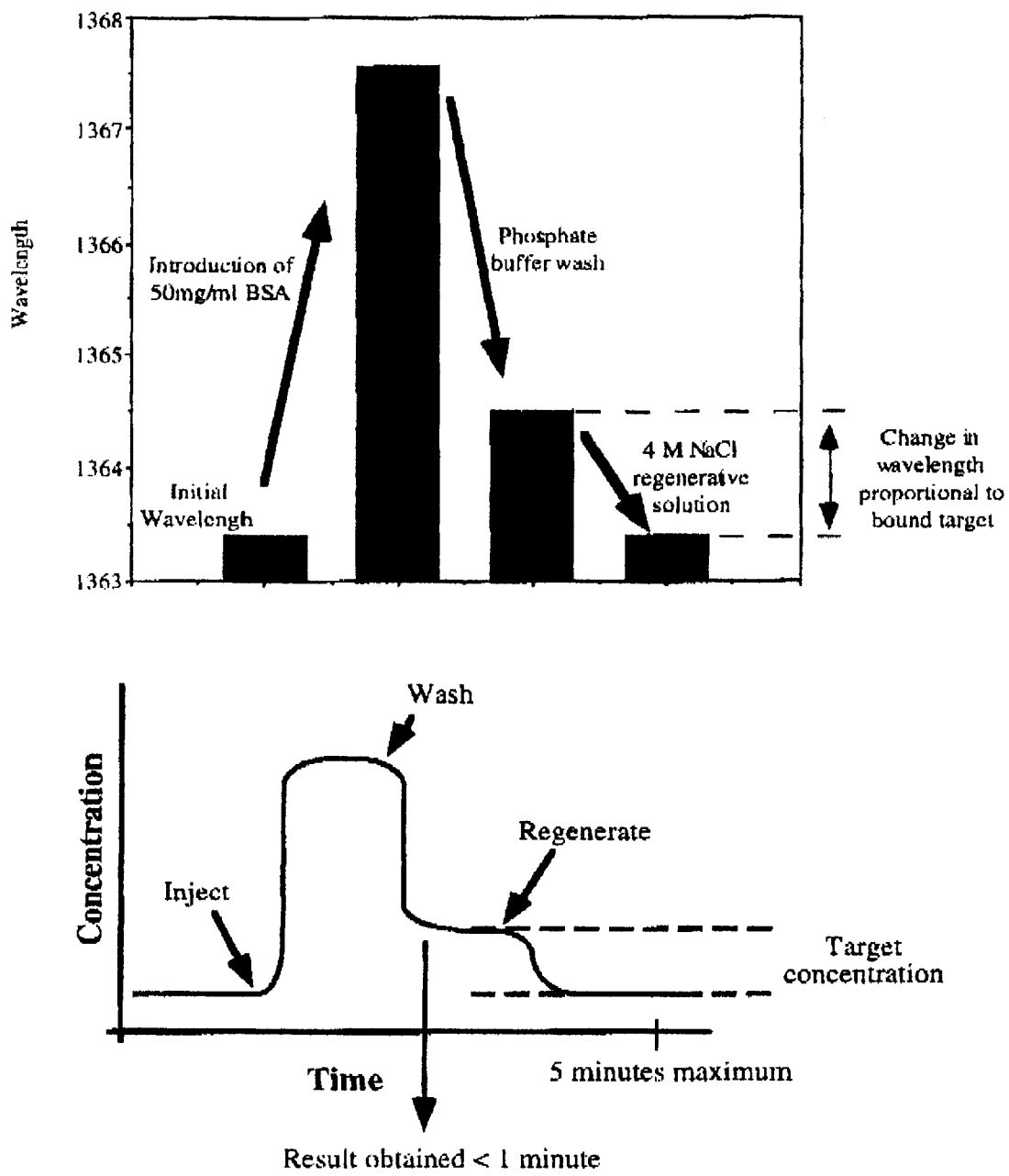
FIG. 5 is a graphical representation of the response of the optical sensor of the present invention.
Figure 6:
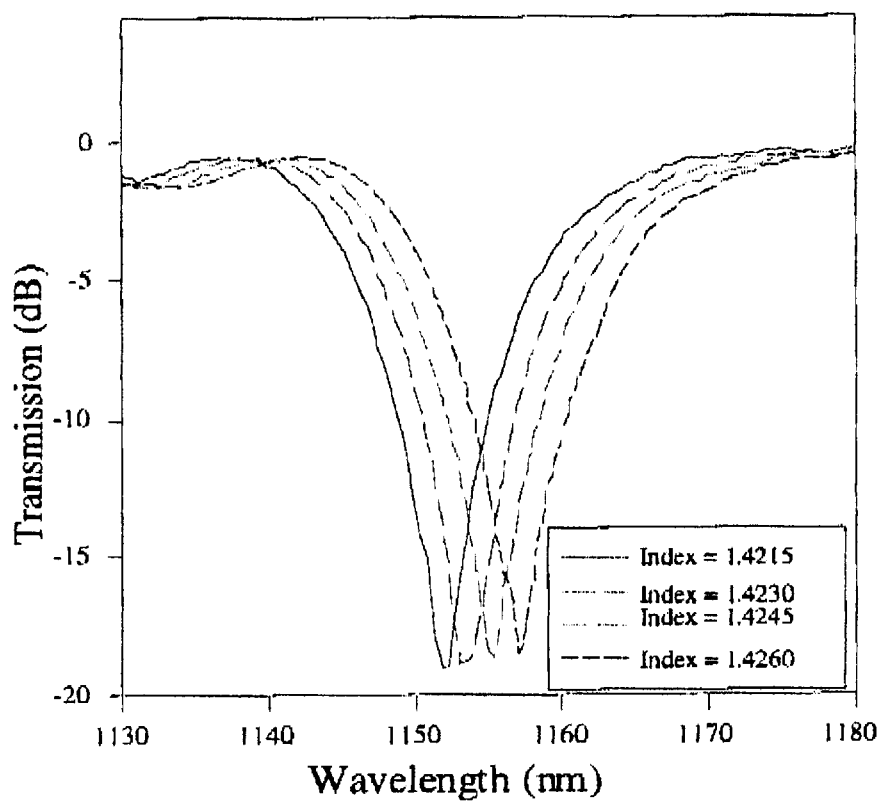
FIG. 6 is the output of the optical sensor of the present invention showing the spectral shifts with respect to refractive index changes.

The fiber was then regenerated with 4M NaCl and 0.5M NaOH. After re-equilibrating the fiber in phosphate buffer, the baseline wavelength of 1363.4 nm was re-established. FIG. 5 shows the response of the sensor due to each reaction and FIG. 6 shows the spectral shifts with respect to the refractive index changes.

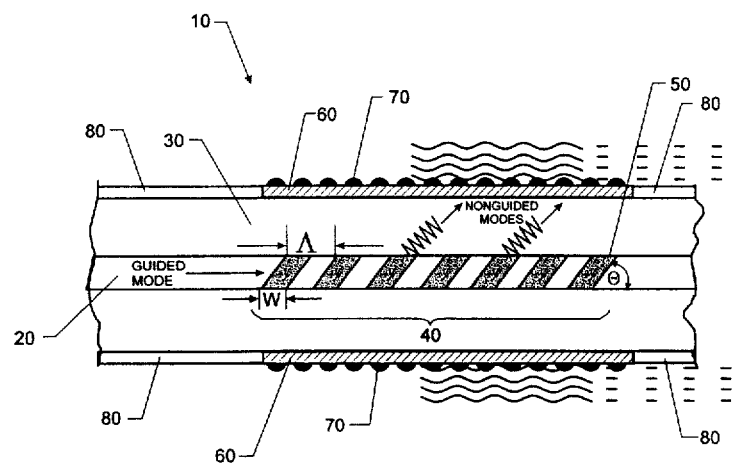

What is claimed is:

1. An optical sensor comprising an optical waveguide, at least one long period grating disposed within the optical waveguide and a reactive coating positioned in an operable relationship to the long period grating wherein the reactive coating causes the long period grating to produce a wavelength transmission spectrum functionally dependent on a parameter sensed.

2. The optical sensor according to claim 1, wherein the reactive coating is selected from the group consisting of: a physically reactive coating, an electronically reactive coating, and a chemically reactive coating.

3. The optical sensor according to claim 1, wherein the optical waveguide is selected from the group consisting of: a planar optical waveguide; an integrated optic waveguide; and a fiber optic waveguide.

4. The optical sensor according to claim 3, wherein the optical waveguide is a fiber optic waveguide having a core, a cladding surrounding the core, and at least one long period grating disposed within the core.

5. The optical sensor according to claim 4, wherein the reactive coating is disposed on the cladding.

6. The optical sensor according to claim 4, wherein the reactive coating is disposed on the core.

7. An optical sensor comprising an optical waveguide, at least one long period grating disposed within the optical waveguide wherein the long period grating has a plurality of index perturbations of width w spaced apart by a periodic distance $\Lambda$ where $10\ \mu m \leq \Lambda \leq 1500\ \mu m$, and a reactive coating positioned in an operable relationship to the long period grating wherein the reactive coating causes the long period grating to produce a wavelength transmission spectrum functionally dependent on a parameter sensed.

8. The optical sensor according to claim 7, wherein the periodic distance $\Lambda$ is irregular.

9. An optical sensor comprising a fiber optic waveguide having a core, a cladding surrounding the core, and at least one long period grating disposed within the core, wherein the long period grating has a plurality of index perturbations of width w spaced apart by a periodic distance $\Lambda$ where $10\ \mu m \leq \Lambda \leq 1500\ \mu m$, and a reactive coating positioned in an operable relationship to the long period grating wherein the reactive coating causes the long period grating to produce a wavelength transmission spectrum functionally dependent on a parameter sensed.

10. The optical sensor according to claim 9, wherein the periodic distance $\Lambda$ is irregular.

11. An optical sensor comprising an optical waveguide, a plurality of long period gratings disposed within the optical waveguide, and a plurality of reactive coatings positioned in an operable relationship to the long period gratings wherein each reactive coating causes each long period grating to produce a wavelength transmission spectrum functionally dependent on each parameter sensed.

12. The optical sensor according to claim 11, wherein the optical waveguide is selected from the group consisting of: a planar optical waveguide; an integrated optic waveguide; and a fiber optic waveguide.

13. The optical sensor according to claim 12, wherein the optical waveguide is a fiber optic waveguide having a core, a cladding surrounding the core and a plurality of long period gratings disposed within the core.

14. The optical sensor according to claim 13, wherein each reactive coating is disposed on the cladding.

15. The optical sensor according to claim 13, wherein each reactive coating is disposed on the core.

16. An optical sensor comprising an optical waveguide, wherein the optical waveguide is a fiber optic waveguide having a core, a cladding surrounding the core and a plurality of long period gratings disposed within the core, wherein each long period grating has a plurality of index perturbations of width w spaced apart by a periodic distance $\Lambda$ where $10\ \mu m \leq \Lambda \leq 1500\ \mu m$; and a plurality of reactive coatings positioned in an operable relationship to the long period gratings wherein each reactive coating causes each long period grating to produce a wavelength transmission spectrum functionally dependent on each parameter sensed.

17. The optical sensor according to claim 16, wherein the periodic distance $\Lambda$ is irregular.

18. An optical sensor comprising an optical waveguide, wherein the optical waveguide is a fiber optic waveguide having a core, a cladding surrounding the core and a plurality of long period gratings disposed within the core; and a plurality of reactive coatings positioned in an operable relationship to the long period gratings wherein each reactive coating causes each long period grating to produce a wavelength transmission spectrum functionally dependent on each parameter sensed and wherein each reactive coating is different.

19. An optical sensor comprising an optical waveguide, a plurality of long period gratings disposed within the optical waveguide wherein each long period grating has a plurality of index perturbations of width w spaced apart by a periodic distance $\Lambda$ where $10\ \mu m \leq \Lambda \leq 1500\ \mu m$; and a plurality of reactive coatings positioned in an operable relationship to the long period gratings wherein each reactive coating causes each long period grating to produce a wavelength transmission spectrum functionally dependent on each parameter sensed.

20. The optical sensor according to claim 19, wherein the periodic distance $\Lambda$ is irregular.

21. The optical sensor according to claim 11, wherein each reactive coating is different.

22. An optical sensor comprising:
a fiber optic waveguide having a core, a cladding surrounding the core, and at least one long period grating disposed within the core; and
a reactive coating disposed on the cladding and positioned in an operable relationship to the long period grating wherein the reactive coating causes the long period grating to produce a wavelength transmission spectrum functionally dependent on a parameter sensed.

23. An optical sensor comprising:
a fiber optic waveguide having a core, a cladding surrounding the core, and a plurality of long period gratings disposed within the core; and
a plurality of reactive coatings, each coating disposed on the cladding and positioned in an operable relationship to each long period grating, wherein each reactive coating causes the long period grating to produce a wavelength transmission spectrum functionally dependent on each parameter sensed.

* * * * *

UNITED STATES PATENT AND TRADEMARK OFFICE
CERTIFICATE OF CORRECTION

PATENT NO. : 5,864,641
DATED : Jan. 26, 1999
INVENTOR(S) : Murphy et al.

It is certified that error appears in the above-identified patent and that said Letters Patent is hereby corrected as shown below:

The title page should be deleted to appear as per attached title page.

Please delete drawing sheets 1-6 and substitute drawing sheets 1-6 as per attached.

Signed and Sealed this

Twenty-fifth Day of May, 1999

*Attest:*

Q. TODD DICKINSON

*Attesting Officer*       *Acting Commissioner of Patents and Trademarks*

United States Patent [19]
Murphy et al.

[11] Patent Number: 5,864,641
[45] Date of Patent: Jan. 26, 1999

[54] OPTICAL FIBER LONG PERIOD SENSOR HAVING A REACTIVE COATING

[75] Inventors: Kent A. Murphy, Troutville; Mark E. Jones, Blacksburg, both of Va.

[73] Assignee: F&S, Inc., Blacksburg, Va.

[21] Appl. No.: 838,873

[22] Filed: Apr. 11, 1997

[51] Int. Cl.[6] .................................. G02B 6/00; G01J 1/04
[52] U.S. Cl. ............................... 385/12; 385/15; 385/37; 385/123; 385/126; 385/127; 385/141; 250/227.14; 250/227.18; 250/227.23
[58] Field of Search .................................. 385/12, 13, 15, 385/37, 123, 125, 126, 127, 141; 250/227.14, 227.18, 227.23

[56] References Cited

U.S. PATENT DOCUMENTS

| | | | |
|---|---|---|---|
| 4,815,843 | 3/1989 | Tiefenthaler et al. | 356/128 |
| 4,929,049 | 5/1990 | Le Goullon et al. | |
| 5,026,139 | 6/1991 | Klainer et al. | |
| 5,047,213 | 9/1991 | Finlan et al. | |
| 5,173,747 | 12/1992 | Bolarski et al. | |
| 5,210,404 | 5/1993 | Cush et al. | 385/37 X |
| 5,253,037 | 10/1993 | Klainer et al. | |
| 5,280,172 | 1/1994 | Di Bin et al. | 250/227.21 |
| 5,324,933 | 6/1994 | Berkcan | 385/12 X |
| 5,359,680 | 10/1994 | Riviere | |
| 5,430,817 | 7/1995 | Vengsarkar | |
| 5,492,840 | 2/1996 | Malmqvist et al. | |
| 5,641,956 | 6/1997 | Vengsarkar et al. | |
| 5,646,400 | 7/1997 | Perez et al. | 250/227.18 |
| 5,647,039 | 7/1997 | Judkins et al. | 385/37 |
| 5,757,540 | 5/1998 | Judkins et al. | 359/341 |

OTHER PUBLICATIONS

V. Bhatia et al., "Optical Fiber Long–Period Grating Sensors," *Lightnews*, Winter 1995, pp. 6–11.

T.A. Tran et al., "Real–time immunoassays using fiber optic long–period grating sensors," *Biomedical Sensing, Imaging, and Tracking Technologies I*, Proceedings SPIE—The International Society for Optical Engineering, R.A. Lieberman et al., Eds., vol. 2676, Jan. 29–31, 1996, pp. 165–170.

A.M. Vengsarkar et al., "Long–Period Fiber Gratings as Gain–Flattening and Laser Stabilizing Devices," *Tenth International Conference on Integrated Optical Fibre Communication*, vol. 5, Jun. 26–30, 1995, pp. 3–4.

A.M. Vengsarkar et al., "Long–Period Fiber Gratings as Band–Rejection Filters," *Journal of Lightwave Technology*, vol. 14, No. 1, Jan. 1996, pp. 58–65.

A.M. Vengsarkar et al., "Long–Period Cladding–Mode––Coupled Fiber Gratings: Properties and Applications," *1995 Technical Digest Series*, vol. 22, Sep. 9–11, 1995, pp. SaB2–1–SaB2–4.

A.M. Vengsarkar et al., "Long–Period Gratings as Band–Rejection Filters," *OFC '95*, Feb. 26–Mar. 3, 1995, pp. PD4–1–PD4–5.

E. Stenberg et al., "Quantitative Determination of Surface Concentration of Protein with Surface Plasmon Resonance Using Radiolabeled Proteins," *Journal of Colloid and Interface Science*, vol. 143, No. 2, May 1991, pp. 513–526.

L. De Maria et al., "Fiber–optic sensor based on surface plasmon interrogation," *Sensors and Actuators*, B. 12, Dec. 21, 1992, pp. 221–223.

R.C. Jorgenson et al., "A fiber–optic chemical sensor based on surface plasmon resonance," *Sensors and Actuators*, B. 12, Dec. 20, 1992, pp. 213–220.

*Primary Examiner*—Brian Healy
*Attorney, Agent, or Firm*—Joy L. Bryant

[57] ABSTRACT

An optical sensor is provided. The optical sensor comprises an optical waveguide, at least one long period grating disposed within the optical waveguide and a reactive coating positioned in an operable relationship to the long period grating wherein the reactive coating causes the long period grating to produce a wavelength transmission spectrum functionally dependent on a parameter sensed. Such sensors may be used to measure physical, electrical and chemical parameters within a single system.

23 Claims, 6 Drawing Sheets